United States Patent [19]

Takaya et al.

[11] Patent Number: 4,739,085
[45] Date of Patent: Apr. 19, 1988

[54] RUTHENIUM-PHOSPHINE COMPLEX

[75] Inventors: Hidemasa Takaya; Tetsuo Ohta; Ryoli Noyori, all of Aichi; Noboru Sayo, Kanagawa; Hidenori Kumobayashi, Kanagawa; Susumu Akutagawa, Kanagawa, all of Japan

[73] Assignee: Takasago Perfumery Co., Ltd., Tokyo, Japan

[21] Appl. No.: 61,770

[22] Filed: Jun. 15, 1987

[30] Foreign Application Priority Data

Aug. 6, 1986 [JP] Japan .................... 61-184651

[51] Int. Cl.$^4$ .................... C07F 15/00; C07F 9/50
[52] U.S. Cl. .................... 556/21; 556/23
[58] Field of Search .................... 556/23, 21

[56] References Cited

U.S. PATENT DOCUMENTS

| | | | |
|---|---|---|---|
| 3,878,122 | 4/1975 | Pennella | 556/23 X |
| 4,268,454 | 5/1981 | Pez et al. | 556/23 X |
| 4,506,030 | 3/1985 | Jones | 556/23 X |
| 4,691,037 | 9/1987 | Yoshikawa et al. | 556/23 X |

*Primary Examiner*—Paul F. Shaver
*Attorney, Agent, or Firm*—Sughrue, Mion, Zinn, Macpeak, and Seas

[57] ABSTRACT

A ruthenium-phosphine complex represented by formula (I):

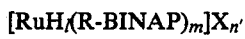

$$[RuH_l(R\text{-}BINAP)_m]X_{n'} \quad (I)$$

wherein R-BINAP is a tertiary phosphine represented by formula (II):

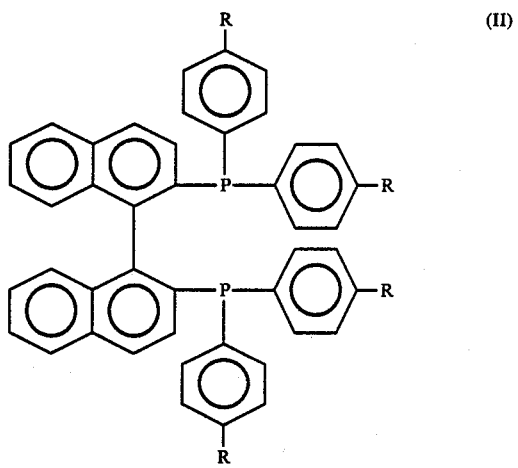

R is a hydrogen atom or a methyl group; X is a ClO$_4$, BF$_4$, or PF$_6$; and when l is 0, then m is 1 and n' is 2, and when l is 1, then m is 2 and n' is 1, is disclosed. The complex is inexpensive and exhibits excellent performances as a catalyst for various organic syntheses, and particularly for asymmetric hydrogenation.

1 Claim, No Drawings

RUTHENIUM-PHOSPHINE COMPLEX

FIELD OF THE INVENTION

The present invention relates to a ruthenium-phosphine complex that can be used as a catalyst not only in various organic syntheses but also in asymmetric syntheses such as asymmetric hydrogenation and asymmetric isomerization.

BACKGROUND OF THE INVENTION

A number of organic synthetic reactions using metal complexes as a catalyst have been developed from old and utilized for many purposes. In particular, many reports have been made on asymmetric catalysts that are used in asymmetric syntheses typified by asymmetric isomerization and asymmetric hydrogenation. Among them, metal complexes composed of metallic rhodium and an optically active tertiary phosphine are well known as a catalyst for asymmetric hydrogenation, and a rhodium-phosphine complex using 2,2'-bis(diphenylphosphino)-1,1'-binaphthyl (hereinafter abbreviated as BINAP) as a ligand is reported in *J. Am. Chem. Soc.*, 102, pp. 7932-7934 (1980). Further, it is reported in Inoue et al., *Chemistry Letters*, pp. 1007-1008 (1985) that asymmetric hydrogenation of geraniol or nerol was performed by using various rhodium-phosphine catalysts to obtain citronellol in an optical yield of 66% ee.

On the other hand, known ruthenium complexes, though there are not so many reports as compared with rhodium complexes, include those having BINAP or 2,2'-bis(di-p-tolylphosphino)-1,1'-binaphthyl (hereinafter abbreviated as T-BINAP) as a ligand, i.e., Ru$_2$Cl$_4$(BINAP)$_2$(NEt$_3$) (wherein Et represents an ethyl group, hereinafter the same) and Ru$_2$Cl$_4$(T-BINAP)$_2$(NEt$_3$), as reported in Ikariya et al, *J. Chem. Soc., Chem. Commun.*, pp. 922 (1985). However, the state-of-the-art ruthenium complexes are not satisfactory in stability as well as optical yield.

Although metallic rhodium provides excellent complex catalysts, it is expensive due to limitations in place and quantity of production. When used as a catalyst component, it forms a large proportion in cost of the catalyst, ultimately resulting in an increase in cost of the final commercial products. While metallic ruthenium is cheaper than rhodium and appears promising as a catalyst component for industrial application, it still has problems in its activity to cope with precision reactions and its range of application.

Therefore, it has been keenly demanded to develop a catalyst which is inexpensive, has high activity and durability, and catalyzes asymmetric reactions to attain high optical yields, i.e., to produce reaction products having high optical purity.

SUMMARY OF THE INVENTION

As a result of extensive investigations with the purpose of meeting the above-described industrial demand, the inventors have discovered a novel ruthenium complex having high catalytic activity, which is usable either for general syntheses when the ligand thereof is optically inactive or for asymmetric syntheses when the ligand thereof is optically active.

The present invention relates to a ruthenium-phosphine complex represented by formula (I):

[RuH$_l$(R-BINAP)$_m$]X$_{n'}$  (I)

wherein R-BINAP is a tertiary phosphine represented by formula (II):

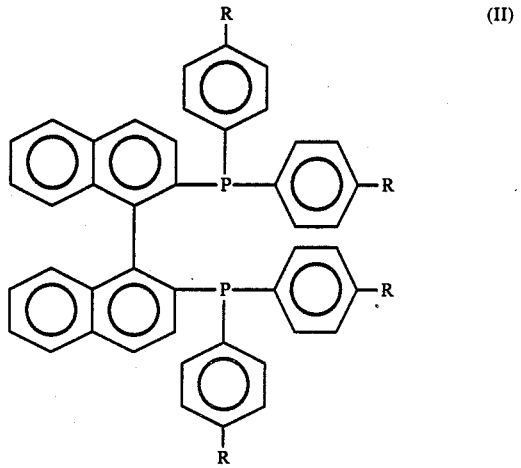

R is a hydrogen atom or a methyl group; X is ClO$_4$, BF$_4$, or PF$_6$; and when l is 0, then m is 1 and n' is 2, and when l is 1, then m is 2 and n' is 1.

DETAILED DESCRIPTION OF THE INVENTION

A ruthenium-phosphine complex of formula (I) wherein l is 0, m is 1, and n' is 2 is produced by reacting, as a starting compound, Ru$_2$Cl$_4$(R-BINAP)$_2$(NEt$_3$) (this compound can be prepaed by the method disclosed in European Pat. No. 174,057A) with a salt represented by formula (III):

MX  (III)

wherein M is a metal selected from the group consisting of Na, K, Li, Mg, and Ag; and X is ClO$_4$, BF$_4$, or PF$_6$, in a solvent composed of water and methylene chloride in the presence of, as a phase transfer catalyst, a quaternary ammonium salt or a quaternary phosphonium salt represented by formula (IV):

R$^1$R$^2$R$^3$R$^4$QZ  (IV)

wherein R$^1$, R$^2$, R$^3$, and R$^4$ are each an alkyl group having from 1 to 16 carbon atoms, a phenyl group, or a benzyl group; Q is nitrogen or phosphorus; and Z is a halogen.

The reaction between Ru$_2$Cl$_4$(R-BINAP)$_2$(NEt$_3$) and the salt of formula (III) is carried out by adding these two compounds and the phase transfer catalyst of formula (IV) in a mixed solvent of water and methylene chloride and stirring the mixture. The salt of formula (III) is used in an amount of from 2 to 10 moles and preferably 5 moles per mole of the ruthenium, and the phase transfer catalyst of formula (IV) is used in an amount of from 1/100 to 1/10 mole per mole of the ruthenium, respectively. It suffices to continue the stirring for a period of time of from 6 to 18 hours and typically 12 hours at a temperature of from 5° to 30° C., and an optimum condition is determined depending on the types of the starting complex and the salt of formula (III) used. It is generally advantageous to mix water and methylene chloride in substantially equal amounts. The salt of formula (III) and the phase transfer catalyst of formula (IV) are added to the reaction system after being dissolved in water.

Examples of the salt of formula (III) include perchlorates, borofluorides, and hexafluorophosphates of Na, K, Li, Mg, or Ag, and they introduce a corresponding anionic group into the ruthenium complex.

Compounds useful as the phase transfer catalyst of formula (IV) are found in documented references, such as W. P. Weber and G. W. Gokel, *Phase Transfer Catalysis in Organic Synthesis*, Springer-Verlag, pp. 6 (1977), including quaternary ammonium salts such as tetramethylammonium bromide, tetrapropylammonium bromide, tetrabutylammonium chloride, tetrabutylammonium iodide, octyltrimethylammonium bromide, lauryltrimethylammonium bromide, lauryltriphenylammonium bromide, cetyltrimethylammonium chloride, methyltrioctylammonium chloride, and benzyltriethylammonium bromide; and quaternary phosphonium salts such as tetrabutylphosphonium chloride, tetrabutylphosphonium bromide, tetrabutylphosphonium iodide, lauryltriethylphosphonium bromide, lauryltributylphosphonium bromide, trioctylethylphosphonium bromide, butyltriphenylphosphonium chloride, and benzyltributylphosphonium bromide. After completion of the reaction, the reaction mixture is allowed to stand, and the methylene chloride solution separated from the aqueous layer is washed and stripped of the methylene chloride by evaporation under vacuum so as to obtain the end product.

Alternatively, the end compound can be synthesized using a complex Ru(R-BINAP)(OAc)$_2$ (wherein Ac is an acetyl group, hereinafter the same) as a starting material, which the present inventors have previously disclosed in Japanese Patent Application No. 108888/1986 (corresponding U.S. Application Ser. No. 38,570, filed Apr. 15, 1987). According to this alternative method, Ru(R-BINAP)(OAc)$_2$ is reacted with an acid represented by the formula (V):

HX         (V)

wherein X is ClO$_4$, BF$_4$, or PF$_6$, under stirring in a mixed solvent of methylene chloride and methanol. The acid of formula (V) is used in an amount of from 2 to 6 moles and preferably 4 moles per mole of the ruthenium. It suffices to continue the stirring for a period of time of from 6 to 18 hours and typically 12 hours at a temperature of from 5° to 30° C., and an optimum condition is determined depending on the types of the starting complex and the acid of formula (V) used. It is generally advantageous to mix methylene chloride and methanol in substantially equal amounts.

A compound of formula (I) wherein l is 1, m is 2, and n' is 1, in which a two-equivalent amount of the R-BINAP is coordinated to the ruthenium metal can be produced by reaction of, as a starting material, RuHCl(R-BINAP)$_2$ (a process of the preparation thereof is disclosed in European Pat. No. 174,057A) with the salt of formula (III) in a mixed solvent of water and methylene chloride in the presence of the phase transfer catalyst of formula (IV). The salt of formula (III) is used in an amount of from 2 to 10 moles and preferably 5 moles per mole of the ruthenium, and the phase transfer catalyst of formula (IV) is used in an amount of from 1/100 to 1/10 mole per mole of the ruthenium. It suffices to continue the stirring for a period of time of from 6 to 18 hours and typically 12 hours at a temperature of from 5° to 30° C., and an optimum condition is determined depending on the types of the starting complex and the salt of formula (III). It is generally advantageous to mix water and methylene chloride in substantially equal amounts. The salt of formula (III) and the phase transfer catalysyt of formula (IV) are added to the reaction system after being dissolved in water.

If an optically active R-BINAP is used as a starting material in each of the methods described above, a ruthenium-phosphine complex of formula (I) having corresponding optically active properties can be produced.

The thus prepared ruthenium-phosphine complex of formula (I)of the present invention exhibits excellent performance when used as a catalyst to be used, for example, in asymmetric hydrogenation. For example, in asymmetric hydrogenation of allyl alcohols such as geraniol and nerol, the ruthenium-phosphine complex of formula (I) of the invention shows a very high catalytic activity even at room temperature. To take geraniol as an example of the substrate, the reaction proceeds rapidly with the complex being present at a molar concentration of from 1/10,000 to 1/50,000 per mole of geraniol to yield citronellol as a hydrogenation product at a selectivity reaching almost 100%. The resulting citronellol has an optical purity of from 96 to 98%. Therefore, the ruthenium-phosphinecomplex of the present invention can be used as an industrial catalyst that ensures very good results.

The present invention is hereunder described in greater detail by way of Referential Examples, Examples, and Use Examples which, however, should not be taken as limiting.

REFERENTIAL EXAMPLE 1

Preparation of Ru$_2$Cl$_4$[(−)-T-BINAP]$_2$NEt$_3$

One gram (3.56 mmoles) of [RuCl$_2$(COD)]$_n$ (the term "COD" is an abbreviation for cycloocta-1,5-diene), 2.9 g (4.27 mmoles) of (−)-T-BINAP, and 1.5 g of triethylamine were added to 50 ml of toluene in a nitrogen atmosphere. The mixture was heated with stirring under toluene refluxing. Six hours later, the reaction mixture was cooled, and the resulting crystal was recovered by filtration. The separated crystal was dissolved in toluene, and recrystallization was effected by gradual addition of diethyl ether. As a result, a purified crystal was obtained in an amount of 2.24 g.

This complex had the following data of elemental analysis except for Ru:

|  | C | H | N | Cl |
| --- | --- | --- | --- | --- |
| Found (%) | 66.4 | 5.3 | 0.73 | 10.5 |
| Calculated (%) | 67.9 | 5.3 | 0.78 | 7.9 |

(NEt$_3$ appearing hereinafter represents triethylamine.)

REFERENTIAL EXAMPLE 2

Preparation of RuHCl[(−)-T-BINAP]$_2$

One gram (3.56 mmoles) of [RuCl$_2$(COD)]$_n$, 5.43 g (8 mmoles) of (−)-T-BINAP, 1.6 g of triethylamine were added to 100 ml of ethanol in a reactor. The contents of the reactor were heated under reflux for 6 hours with stirring in a nitrogen atmosphere. After completion of the reaction, the ethanol was distilled off, and the residue was dissolved in 40 ml of dichloromethane, with the insoluble matter being filtered off. The filtrate was recrystallized by gradual addition of diethyl ether. Upon vacuum drying, a purified crystal was obtained in an amount of 3.4 g.

REFERENTIAL EXAMPLE 3

Preparation of Ru[(−)-BINAP](O$_2$CCH$_3$)$_2$

A 250-ml Schlenk-tube was charged with 1.43 g (0.9 mmole) of the Ru$_2$Cl$_4$[(−)-BINAP]$_2$(NEt$_3$) that was prepared by the process as disclosed in European Pat. No. 174,057A and 3.06 g (37 mmoles) of sodium acetate. After the atmosphere in the tube had been thoroughly displaced with nitrogen, 100 ml of t-butanol was added thereto, and the mixture was heated under reflux for 12 hours. After completion of the reaction, the t-butanol was distilled off at 20 mmHg, and the resulting dry solid was extracted twice with 10-ml portions of diethyl ether. After distilling off the diethyl ether, the resulting dry solid was further extracted twice with 10-ml portions of ethanol. The extract was concentrated to dryness to obtain 1.5 g of crude Ru[(−)-BINAP]-(O$_2$CCH$_3$)$_2$. Recrystallization from ethyl acetate gave a yellowish brown solid in an amount of 0.79 g (yield: 52%).

Melting point: 180° to 181° C. (with decomposition)
Elemental analysis for C$_{48}$H$_{38}$O$_4$P$_2$Ru:

|  | Ru | P | C | H |
|---|---|---|---|---|
| Found (%) | 11.85 | 7.28 | 68.35 | 4.61 |
| Calculated (%) | 12.01 | 7.36 | 68.48 | 4.55 |

EXAMPLE 1

Preparation of [Ru((−)-T-BINAP)](BF$_4$)$_2$
([2,2′-Bis(di-p-tolylphosphino)-1,1′-binaphthyl]ruthenium-ditetrafluoroborate)

A 250-ml Schlenk-tube was charged with 0.54 g (0.3 mmole) of the Ru$_2$Cl$_4$[(−)-T-BINAP]$_2$NEt$_3$ as prepared in Referential Example 1. After the atmosphere in the tube had been thoroughly displaced with nitrogen, 60 ml of methylene chloride was added thereto, followed by addition of 0.66 g (6.0 mmoles) of sodium tetrafluoroborate in 60 ml of water and 16 mg (0.06 mmole) of triethylbenzylammonium bromide in 3 ml of water. Reaction was performed by stirring the contents for 12 hours at room temperature. After completion of the reaction, the reaction mixture was allowed to stand, and the methylene chloride solution separated from the aqueous layer was washed with 50 ml of water. After liquid separation, the methylene chloride was distilled off under vacuum, and the residue was vacuum-dried to obtain a dark brown solid of [Ru((−)-T-BINAP)](BF$_4$)$_2$ in an amount of 0.55 g (yield: 95.8%).

Elemental analysis for C$_{48}$H$_{40}$B$_2$F$_8$P$_2$Ru:

|  | Ru | P | C | H |
|---|---|---|---|---|
| Found (%) | 10.18 | 6.31 | 60.21 | 4.39 |
| Calculated (%) | 10.60 | 6.50 | 60.47 | 4.23 |

Instrumental analysis of $^{31}$P nuclear magnetic resonance spectrum (hereinafter abbreviated as $^{31}$P NMR) was conducted with a Model JNM-GX400 (161 MHz) of JEOL Ltd., with chemical shifts being determined with 85% phosphoric acid used as an external standard. The results are shown below.

$^{31}$P NMR (CDCl$_3$) δppm: 12.823 (d, J=41.1 Hz); 61.390 (d, J=41.0 Hz).

EXAMPLE 2

Preparation of [RuH((−)-T-BINAP)$_2$]BF$_4$ ([Hydride Bis[2,2′-bis(di-p-tolylphosphino)-1,1′-binaphthyl]ruthenium-tetrafluoroborate)

A Shlenk-tube was charged with 1.15 g (0.77 mmole) of the RuHCl[(−)-T-BINAP]$_2$ as prepared in Referential Example 2. After the atmosphere in the tube had been thoroughly displaced with nitrogen, 75 ml of methylene chloride was added thereto, followed by addition of 0.85 g (7.7 mmoles) of sodium tetrafluoroborate in 75 ml of water and 21 mg (0.08 mmoles) of triethylbenzylammonium bromide in 4 ml of water. Reaction was performed by stirring the contents for 12 hours at room temperature. After completion of the reaction, the reaction mixture was allowed to stand, and the methylene chloride solution separated from the aqueous layer was washed with 50 ml of water. After liquid separation, the methylene chloride was distilled off under vacuum, and the residue was vacuum-dried to obtain a dark brown solid of [RuH((−)-T-BINAP)$_2$]BF$_4$ in an amount of 1.16 g (yield: 97.0%).

Elemental analysis for C$_{96}$H$_{81}$BF$_4$P$_4$Ru:

|  | Ru | P | C | H |
|---|---|---|---|---|
| Found (%) | 6.13 | 7.76 | 74.08 | 5.61 |
| Calculated (%) | 6.54 | 8.01 | 74.56 | 5.28 |

$^{31}$P NMR (CDCl$_3$) δppm: 33.546 (s); 36.876 (s).

EXAMPLE 3

Preparation of [Ru((−)-BINAP)](BF$_4$)$_2$
([2,2′-Bis(diphenylphosphino)-1,1′-binaphthyl]ruthenium-ditetrafluoroborate)

A Shlenk-tube was charged with 0.51 g (0.61 mmole) of Ru[(−)-BINAP](O$_2$CCH$_3$)$_2$ as prepared in Referential Example 3. After the atmosphere in the tube had been thoroughly displaced with nitrogen, 7 ml of methylene chloride, 7 ml of methanol, and 0.52 ml (2.48 mmoles) of an aqueous solution of 42% borofluoric acid were added thereto, and the mixture was stirred for 12 hours at room temperature. Thereafter, the reaction mixture was concentrated under vacuum to obtain a yellowish brown solid of [Ru((−)-BINAP)](BF$_4$)$_2$ in an amount of 0.53 g (yield: 97.2%).

Elemental anslysis for C$_{44}$H$_{32}$B$_2$F$_8$P$_2$Ru:

|  | Ru | P | C | H |
|---|---|---|---|---|
| Found (%) | 10.88 | 6.51 | 58.62 | 3.82 |
| Calculated (%) | 11.26 | 6.90 | 58.90 | 3.59 |

$^{31}$P NMR (CDCl$_3$) δppm: 10.357 (d, J=48.9 Hz); 77.450 (d, J=48.9 Hz).

EXAMPLES 4 TO 9

The results of Examples 4 to 9 are summarized in Table 1. Except for the types of the starting ruthenium-phosphine complex and the salt of formula (III), the compounds of Examples 4 to 6 were synthesized in accordance with Example 1, and those of Examples 7 to 9 in accordance with Example 2, respectively.

TABLE 1

| Example No. | Compound of the Invention (empirical formula) | Element | Calcd. | Found | $^{31}$P NMR δ value |
|---|---|---|---|---|---|
| 4 | [Ru((−)-BINAP)](ClO$_4$)$_2$ | Ru | 10.95 | 10.56 | 10.451 (d, J = 41.1 Hz) |
|   |   | P | 6.71 | 6.52 | 77.456 (d, J = 41.1 Hz) |
|   |   | C | 57.28 | 56.71 |   |
|   | (for C$_{44}$H$_{36}$Cl$_2$O$_8$P$_2$Ru) | H | 3.50 | 3.88 |   |
| 5 | [Ru((−)-T-BINAP)](ClO$_4$)$_2$ | Ru | 10.32 | 10.08 | 12.920 (d, J = 41.1 Hz) |
|   |   | P | 6.33 | 5.97 | 61.402 (d, J = 41.1 Hz) |
|   |   | C | 58.90 | 58.61 |   |
|   | (for C$_{48}$H$_{40}$Cl$_2$O$_8$P$_2$Ru) | H | 4.12 | 4.53 |   |
| 6 | [Ru((−)-T-BINAP)](PF$_6$)$_2$ | Ru | 9.45 | 9.18 | 12.811 (d, J = 41.1 Hz) |
|   |   | P | 11.58 | 11.27 | 61.390 (d, J = 41.1 Hz) |
|   |   | C | 53.89 | 53.62 |   |
|   | (for C$_{48}$H$_{40}$F$_{12}$P$_4$Ru) | H | 3.77 | 4.08 |   |
| 7 | [RuH((−)-BINAP)$_2$]BF$_4$ | Ru | 7.04 | 6.67 | 32.004 (s) |
|   |   | P | 8.64 | 8.14 | 35.334 (s) |
|   |   | C | 73.70 | 72.81 |   |
|   | (for C$_{88}$H$_{65}$BF$_4$P$_4$Ru) | H | 4.57 | 4.91 |   |
| 8 | [RuH((−)-T-BINAP)$_2$]ClO$_4$ | Ru | 6.48 | 6.13 | 33.559 (s) |
|   |   | P | 7.95 | 7.66 | 36.889 (s) |
|   |   | C | 73.96 | 73.61 |   |
|   | (for C$_{96}$H$_{81}$ClO$_4$P$_4$Ru) | H | 5.24 | 5.57 |   |
| 9 | [RuH((−)-T-BINAP)$_2$]PF$_6$ | Ru | 6.30 | 5.97 | 33.619 (s) |
|   |   | P | 9.65 | 9.47 | 36.810 (s) |
|   |   | C | 71.86 | 71.52 |   |
|   | (for C$_{96}$H$_{81}$F$_6$P$_5$Ru) | H | 5.09 | 5.42 |   |

USE EXAMPLE 1

A 200-ml autoclave was charged with 62 g (0.4 mole) of geraniol and 75 ml of oxygen-free methanol, and 7.8 mg (0.008 mmole) of the [Ru((−)-T-BINAP)](ClO$_4$)$_2$ as prepared in Example 5 was added under a nitrogen stream to effect hydrogenation at 20° C. for 15 hours at a hydrogen pressure of 30 kg/cm$^2$. After the solvent had been distilled off, the residue was subjected to distillation to obtain 61.8 g of a fraction having a boiling point of 108° C./100 mmHg. This fraction was found to contain 99.9% citronellol by gas chromatography with a silica capillary ("OV-101" of Gasukuro Kogyo Inc.) of 0.25 mmφ and 25 m$^L$ with the temperature increased from 100° to 250° C. at a rate of 3° C./min. The specific rotation ([α]$_D^{25}$) of the citronellol was +5.19° (c=19.8, chloroform).

The citronellol was converted to citronellic acid by Jones' oxidation, which was then reacted with R-(+)-1-(1-naphthyl)ethylamine to synthesize its amide form. The amide was subjected to analysis of diastereomers by high-performance liquid chromatography on a Chemopack (a column of Chemco Co., Ltd.) packed with Nucleosil 100-3 (a carrier of Chemco Co., Ltd.; 4.6 mmφ×300 mm$^L$) that was eluted with a hexane/diethyl ether (7:3 by volume) mixture at a flow rate of 1 ml/min. UV detection was conducted at 254 nm. The analysis showed that the starting alcohol was a mixture of 97.5% of (R)-(+)-citronellol and 2.5% of (S)-(−)-citronellol, indicating that the optical yield of the reaction was 95% ee.

USE EXAMPLES 2 TO 9

Using ruthenium-phosphine complexes prepared in accordance with the present invention, asymmetric hydrogenation of geraniol was conducted by repeating the procedures of Use Example 1. The results are shown in Table 2.

TABLE 2

| Use Example No. | Compound of the Invention | Substrate/ Catalyst Molar Ratio | Reaction Condition | | | Results | | |
|---|---|---|---|---|---|---|---|---|
| | | | Hydrogen Pressure (kg/cm$^2$) | Temperature (°C.) | Time (hr) | Conversion (%) | Optical Yield (% ee) | Selectivity to Citronellol (%) |
| 2 | [Ru((−)-BINAP)](ClO$_4$)$_2$ | 10000/1 | 30 | 20 | 8.1 | 99.3 | 95.8 | 99.8 |
| 3 | [Ru((−)-BINAP)](BF$_4$)$_2$ | 10000/1 | 30 | 20 | 4.5 | 99.2 | 96.1 | 99.7 |
| 4 | [Ru((−)-T-BINAP)](BF$_4$)$_2$ | 10000/1 | 30 | 20 | 3.0 | 99.5 | 97.2 | 99.6 |
| 5 | [Ru((−)-T-BINAP)](PF$_6$)$_2$ | 10000/1 | 30 | 20 | 3.5 | 99.7 | 94.8 | 99.6 |
| 6 | [RuH((−)-BINAP)$_2$]BF$_4$ | 5000/1 | 30 | 20 | 26.5 | 97.8 | 93.6 | 99.5 |
| 7 | [RuH((−)-T-BINAP)$_2$]BF$_4$ | 5000/1 | 30 | 20 | 30 | 98.2 | 94.2 | 99.8 |
| 8 | [RuH((−)-T-BINAP)$_2$]ClO$_4$ | 5000/1 | 30 | 20 | 26 | 97.9 | 94.6 | 99.7 |
| 9 | [RuH((−)-T-BINAP)$_2$]PF$_6$ | 5000/1 | 40 | 30 | 32 | 98.5 | 93.5 | 99.8 |

As is apparent from the foregoing description and experimental results, the present invention provides a novel ruthenium-phosphine complex that exhibits a superior performance when used as a catalyst for a variety of organic syntheses including asymmetric hydrogenation. This complex achieves industrially satisfactory results in terms of selective hydrogenation of olefins and catalytic activity for attaining it. In addition, the complex of the present invention can be manufactured at a lower cost than the conventional rhodium catalysts, to thereby contribute to a reduction in the price of the product manufactured by using the complex as a catalyst.

While the invention has been described in detail and with reference to specific embodiments thereof, it will be apparent to one skilled in the art that various changes and modifications can be made therein without departing from the spirit and scope thereof.

What is claimed is:

1. A ruthenium-phosphine complex represented by formula (I):

[RuH$_l$(R-BINAP)$_m$]X$_{n'}$     (I)
wherein R-BINAP is a tertiary phosphine represented by formula (II):
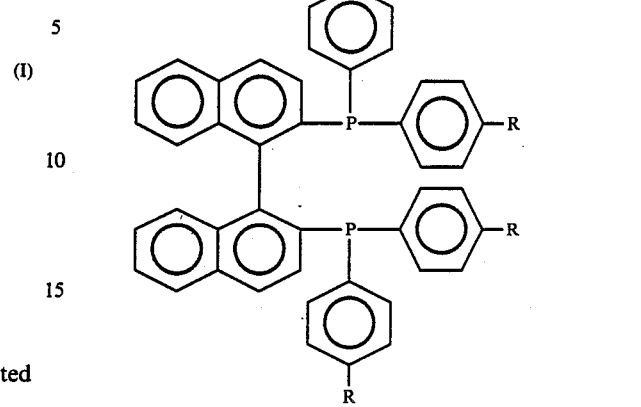
R is a hydrogen atom or a methyl group; X is ClO$_4$, BF$_4$, or PF$_6$; and when l is 0, then m is 1 and n' is 2, and when l is 1, then m is 2 and n' is 1.
* * * * *